US005757671A

United States Patent [19]
Drevillon et al.

[11] Patent Number: 5,757,671
[45] Date of Patent: May 26, 1998

[54] MULTI-DETECTOR ELLIPSOMETER AND PROCESS OF MULTI-DETECTOR ELLIPSOMETRIC MEASUREMENT

[75] Inventors: Bernard Drevillon, Meudon; Jean-Yves Parey, La Ville Du Bois, both of France

[73] Assignee: Centre National de la Recherche Scientifique, Paris, France

[21] Appl. No.: 692,197

[22] Filed: Aug. 5, 1996

[30] Foreign Application Priority Data

Aug. 3, 1995 [FR] France ................... 95 09478

[51] Int. Cl.⁶ ................... G01N 21/62; G01B 9/027
[52] U.S. Cl. ................... 364/525; 356/366; 356/367; 356/368; 356/369; 250/225
[58] Field of Search ................... 364/525; 356/364, 356/367, 369, 345, 349, 300, 318, 432, 366, 368; 250/225, 226, 559.22, 559.27, 559.49; 370/484, 464

[56] References Cited

U.S. PATENT DOCUMENTS

| | | | |
|---|---|---|---|
| 4,884,265 | 11/1989 | Schroeder et al. | 370/484 |
| 5,042,951 | 8/1991 | Gold et al. | 356/369 |
| 5,166,752 | 11/1992 | Spanier et al. | 356/369 |
| 5,196,903 | 3/1993 | Masutani | 356/346 |
| 5,329,357 | 7/1994 | Bernoux et al. | 356/369 |
| 5,408,322 | 4/1995 | Hsu et al. | 356/369 |
| 5,412,473 | 5/1995 | Rosencwaig et al. | 356/351 |
| 5,485,271 | 1/1996 | Drevillon et al. | 356/345 |
| 5,536,936 | 7/1996 | Drevillon et al. | 250/226 |

FOREIGN PATENT DOCUMENTS 0 663 590   7/1995   European Pat. Off.

OTHER PUBLICATIONS

"Progess in Crystal Growth and Characterization of Materials", 1993, vol. 27, No. 1, pp. 12–14.

"Phase–Modulated Ellipsometer Using a Fourier Transform Infrared Spectrometer of Real Time Applications", by Canillas et al., Review of Scientific Instruments, vol. 64, No. 8, Aug. 1993, pp. 2153–2159.

"An IR Phase–Modulated Ellipsometer Using a Fourier Transform Spectrometer for In Situ Applications", by Canillas et al., Thin Solid Films, vol. 234, No. Jan. 2, Oct. 1993, pp. 318–322.

Primary Examiner—James P. Trammell
Assistant Examiner—Tuan Q. Dam
Attorney, Agent, or Firm—Reid & Priest LLP

[57] ABSTRACT

An ellipsometer comprising several photodetectors and an electronic processing unit (4) produces a beam of light modulated at a modulation frequency (Fm) which is reflected by a sample. The photodetectors measure fluxes from parts of the reflected luminous beam, producing measured analog signals in input channels (6), and the electronic processing unit (4) calculates physical parameters of the sample. This electronic processing unit (4) comprises a multiplexing and digitizing unit (7) successively switching to the input channels (6) at a switching frequency (Fe) and a sequencer (19). The sequencer (19) comprises means (24, 35) to allow setting the switching frequency (Fe) as a multiple of the modulation frequency (Fm). The ellipsometer takes optical measurements in real time, in particular for depositing films on substrates.

14 Claims, 3 Drawing Sheets

5,757,671

MULTI-DETECTOR ELLIPSOMETER AND PROCESS OF MULTI-DETECTOR ELLIPSOMETRIC MEASUREMENT

BACKGROUND OF THE INVENTION

1. Field of the Invention

This invention relates to a multi-detector ellipsometer and a process of multi-detector ellipsometric measurement.

2. Related Art

Ellipsometry is a non-destructive measurement technique allowing the optical characterization of a sample disposing of a specular or quasi-specular surface.

This measurement is usually carried out in oblique incidence but may also be performed in normal incidence, in which case ellipsometry is called Reflexion Anisotropy Spectroscopy (RAS) or Reflectance Difference Spectroscopy (RDS).

Ellipsometry may also be extended to rough surfaces or to the diffusion of light by particles of a physical system.

In general terms, the technique is based on the determination of the Mueller matrix of the sample or the physical system.

Ellipsometry may be applied in situ to allow the study of the growth mechanisms of thin films, of interface formation and the control of elaboration processes of these films and interfaces. Ellipsometry is, for example, used in the study and control of the manufacture of semi-conductors.

Ellipsometric measurements may be carried out at a fixed wavelength, or at several wavelengths (spectroscopic ellipsometry). Depending on the domain of the source wavelength—near ultra-violet, visible, near infra-red, infra-red, etc.—it is possible to gain access to different properties of films and materials or to explore different materials.

In the ultra-violet and visible domain, the depth of penetration of the radiation is often weak. This furnishes favorable conditions for the study of surfaces and interfaces, and for controls in real time. It does not as a rule allow access to the volumic properties of the films and materials which may, on the contrary, be obtained by measurements in the infra-red domain. Infra-red is well suited to vibrational measurements of absorption (chemical bonding).

For ellipsometric measurements, the surface of a sample is lit by a luminous beam and the polarization state of an incident beam is compared to that of the reflected or transmitted beam. The beam reflected or transmitted by the sample will be referred to as the returned beam.

The ellipsometric measurements may be carried out in the presence of an alternating external excitation, for example of an optical, electrical or magnetic type, the corresponding techniques being known respectively as photo-ellipsometry, electro-ellipsometry and magneto-ellipsometry.

The polarization state of the returned beam depends at one and the same time on the properties of the sample, the incidence angle of the incident beam, and the measurement wavelength. The relation between this polarization state and these parameters is given by the Fresnel equations cited, for example, by D. CHARLOT and A. MARUANI in Appl. Opt. 24, 3368, 1985.

In a phase-modulated ellipsometer, an incident ray has its polarization modulated by a phase difference generated between two proper axes of a phase modulator.

Typically, the phase shift evolves with time t according to a periodic law of modulation frequency Fm, this phase shift being proportional to the sine first order ($2 \pi$ Fm t). In a phase-modulated ellipsometer, the intensity of a flux of a luminous beam reflected by a sample makes it possible to deduce, in a known way, the modifications of the polarization state of the luminous beam.

Ellipsometry, and more especially spectroscopic phase-modulated ellipsometry (SPME), is an effective technique for measuring the growth of films on a substrate in real time. This technique has the advantage of not perturbing ongoing reactions. It is also very sensitive to such physical parameters of the measured sample as a film thickness and a refraction index. Moreover, it allows fast measurements.

According to the standard technique, a spectroscopic phase-modulated ellipsometer includes a single photodetector measuring a luminous flux reflected by a sample. The recording of a spectre then requires the scanning of a dispersive system, such as a prism or a network, over periods of time lasting as much as several tens of seconds. This ellipsometer is therefore ill-suited to measurements in real time of rapidly evolving phenomena.

To accelerate the measurement process, an ellipsometer has been proposed comprising a spectrograph and several photodetectors, in addition to an electronic processing unit. An illustration of such an ellipsometer with 4 photodetectors is provided by B. DREVILLON in "Progress in Crystal Growth and Characterization of Materials", vol. 27, num. 1, pp. 1–87, 1993 (pages 14 and 15). The photodetectors are adjusted to the spectrograph in such a way as to measure fluxes of a luminous beam reflected by a sample and broken down by the spectrograph. The photodetectors, linked to the electronic processing unit by connections or input channels, produce measured signals in the input channels, from which said signals the electronic processing unit calculates the physical parameters of the sample. To this end, the electronic processing unit is synchronized with the phase modulator and carries out operations associated successively with the different input channels, according to acquisition phases possibly of the same duration. The duration of the acquisition phases is a multiple of the modulation period Tm, equal to the inverse of the modulation frequency Fm. During any one of the acquisition phases, the electronic processing unit receives a measured signal from one of the input channels. It then switches to another input channel in order to move on to the next acquisition phase. The ellipsometer thus makes use of a so-called sequential-mode acquisition technique.

This multi-detector ellipsometer makes it possible to exploit several wavelengths of the reflected luminous beam more efficiently and more quickly than a standard ellipsometer comprising a single photodetector. Nevertheless, these possibilities remain noticeably inadequate in relation to the requirements inherent in real-time measurements.

In particular, it is difficult to extend the sequential mode to a large number of photodetectors, for example several tens, due to the time required to scan all the input channels.

SUMMARY OF THE INVENTION

This invention relates to a multi-detector spectroscopic phase-modulated ellipsometer allowing a considerable acceleration of measurements in real time compared to existing devices.

More specifically, the invention relates to a spectroscopic ellipsometer which allows the quasi-simultaneous acquisition of a large number of wavelengths, this acquisition reducing considerably the duration of a cycle.

The invention also relates to a multi-detector ellipsometer allowing quasi-simultaneous acquisitions in several points of the sample.

It also relates to a multi-detector ellipsometer allowing quasi-simultaneous acquisitions for several polarization states of a luminous beam diffused by a sample.

In a more general application, the invention relates to a multi-detector ellipsometer allowing the reading in parallel of a large number of photodetectors.

The invention also relates to a fast process of multi-detector ellipsometric measurement, applicable to quasi-simultaneous measurements of several items of information in real time.

In this connection, the invention relates to a multi-detector ellipsometer comprising:

at least one luminous source emitting at least one incident luminous beam, at least one polarizer polarizing this incident luminous beam, at least one polarization modulator generating a polarization modulation at a modulation frequency Fm of the luminous beam of polarized light, means of lighting a sample by the incident luminous beam producing a returned luminous beam having a polarization state, at least one analyzer analyzing the polarization state of the returned luminous beam, at least two photodetectors measuring fluxes of parts of the returned luminous beam and producing measured analog signals in input channels, at least one electronic processing unit linked to the input channels, calculating physical parameters of the sample from the measured analog signals.

This electronic processing unit includes:

at least one multiplexing and digitization unit, multiplexing and converting the measured analog signals into a multiplexed digital signal, the multiplexing and digitization unit switching successively on the input channels at a switching frequency, a digital signal processing unit linked to the multiplexing and digitization unit, dissociating the multiplexed digital signal into components corresponding respectively to the input channels and applying to these components discrete Fourier transforms in order to extract Fourier parameters corresponding to the modulation frequency Fm and its multiples, a final calculating unit linked to the digital signal processing unit, calculating the physical parameters from the Fourier parameters, a sequencer linked to the multiplexing and digitization unit, and to the digital signal processing unit, this sequencer sending synchronization signals.

According to the invention, the sequencer includes means making it possible to insist that the switching frequency Fe is a multiple of the modulation frequency Fm.

In known multi-detector ellipsometers, for which a sequential-mode acquisition is applied, a switching is performed at the end of each acquisition phase. Given that the time Ta of the acquisition phase is a multiple of the modulation period Tm, the switching frequency Fe is a divisor of the modulation frequency Fm. On the contrary, in the invention, the switching frequency Fe is a multiple of the modulation frequency Fm. Thus the electronic processing unit switches several times from one input channel to another during each of the modulation periods Tm.

The information from the different photodetectors is not acquired sequentially but in crossed fashion. The reading of the photodetectors by the electronic processing unit therefore includes operations in parallel.

Thanks to its speed of acquisition, the ellipsometer according to the invention is particularly suited to real-time measurements of physical phenomena.

In general, the sample studied is constituted of a non-transparent material. The incident luminous beam is then reflected by the sample. However, it is possible to study samples constituted of transparent materials by transmission of the incident luminous beam through the sample, without leaving the domain of ellipsometry.

Preferentially, the multiplexing and digitization unit producing values of the multiplexed digital signal in sampling points, the switching frequency is equal to the modulation frequency multiplied by the number of input channels and by the number of sampling points per input channel and per modulation period.

The configuration of the multi-detector ellipsometer obtained in this way bestows optimum efficiency and speed on the ellipsometer. Indeed, at each modulation period Tm, the electronic processing unit scans all the input channels. It thus acquires in parallel, and quasi-simultaneously, information from all the photodetectors.

In an advantageous embodiment of the ellipsometer according to the invention, the multiplexing and digitization unit comprises a multiplexer linked to the input channels and a digitizer linked to the multiplexer, the multiplexer multiplexing the analog signals measured in a multiplexed analog signal by switching successively on the input channels, and the digitizer converting the multiplexed analog signal into a multiplexed digital signal.

The advantage of this solution is that it requires only one digitizer, thereby making this embodiment inexpensive and easy to carry out.

The separation of the multiplexer and the digitizer can be purely theoretical since the two functions can be incorporated into a single material element.

The electronic processing unit advantageously comprises a first calculating unit linked to the digitizer and to the digital signal processing unit, this first calculating unit performing a preliminary filtering of the multiplexed digital signal, by integration on several modulation periods.

The acquisition and processing of the data acquired during these modulation periods Tm constitute a cycle of the ellipsometer according to the invention.

It is useful that the ellipsometer according to the invention includes means of supplementary external excitation of the sample capable of generating a supplementary modulation at an excitation frequency which is distinct from the polarization modulation frequency.

In a first advantageous embodiment of the ellipsometer according to the invention, said ellipsometer comprises a clock external to the electronic processing unit generating the modulation frequency and a frequency multiplication system. The external clock is linked to the sequencer through the intermediary of the frequency multiplication system, and the sequencer produces the switching frequency from the modulation frequency.

In a second advantageous embodiment of the ellipsometer according to the invention, the electronic processing unit comprises an internal clock generating the modulation and switching frequencies.

This internal clock is typically used with an electro-optical modulator.

Preferentially, the electronic processing unit comprises at least one printed circuit board, this board preferentially including at least one field programmable gate array.

It is also advantageous for the ellipsometer according to the invention to comprise a pre-processing memory disposed between the multiplexing and digitization unit and the digital signal processing unit. This pre-processing memory stores the multiplexed digital signal for at least one modulation period and then restores it to the digital signal processing unit.

Moreover, the ellipsometer according to the invention advantageously comprises a user interface allowing the connection of the electronic processing unit to a communication network.

The invention also relates to a multi-detector ellipsometric measuring process of physical parameters of a sample. In this process:

at least one incident luminous beam is emitted by at least one luminous source, the incident luminous beam is polarized by at least one polarizer, the incident luminous beam is modulated at a modulation frequency by at least one polarization modulator, the sample is lit with the incident luminous beam, the sample producing a returned luminous beam having a polarization state, the polarization state of the returned luminous beam is analyzed by at least one analyzer, the fluxes of parts of the returned luminous beam are measured by at least two photodetectors, and the measured analog signals from the photodetectors are produced in input channels, operations are performed by an electronic processing unit on the measured analog signals in order to deduce the physical parameters.

These operations consist of:

multiplexing and converting the measured analog signals into a multiplexed digital signal, by means of a multiplexing and digitization unit, by switching the multiplexing and digitization unit successively on the input channels at a switching frequency, dissociating the multiplexed digital signal into components corresponding respectively to the input channels, and applying to these components Fourier transforms from which Fourier parameters are extracted, calculating the physical parameters from the Fourier parameters.

According to the invention, the switching frequency is a multiple of the modulation frequency, so that on leaving the multiplexing and digitization unit, the components are interlaced in the multiplexed digital signal.

In a first preferred embodiment of the process according to the invention, the parts of the returned luminous beam reaching the photodetectors are produced by a spectral decomposition in wavelength.

In a second preferred embodiment of the process according to the invention, the parts of the returned luminous beam reaching the photodetectors are produced by a spatial decomposition and come from different zones of the sample.

In a third preferred embodiment of the process according to the invention, the parts of the returned luminous beam reaching the photodetectors are produced by a decomposition into different polarization states.

In all cases, the ellipsometric measurement may be carried out in the presence of a modulated supplementary external excitation.

BRIEF DESCRIPTION OF THE DRAWINGS

A clearer understanding of this invention will emerge from an example of an application and implementation with reference to the accompanying drawings in which.

DETAILED DESCRIPTION OF THE PREFERRED EMBODIMENTS

Figure 1:
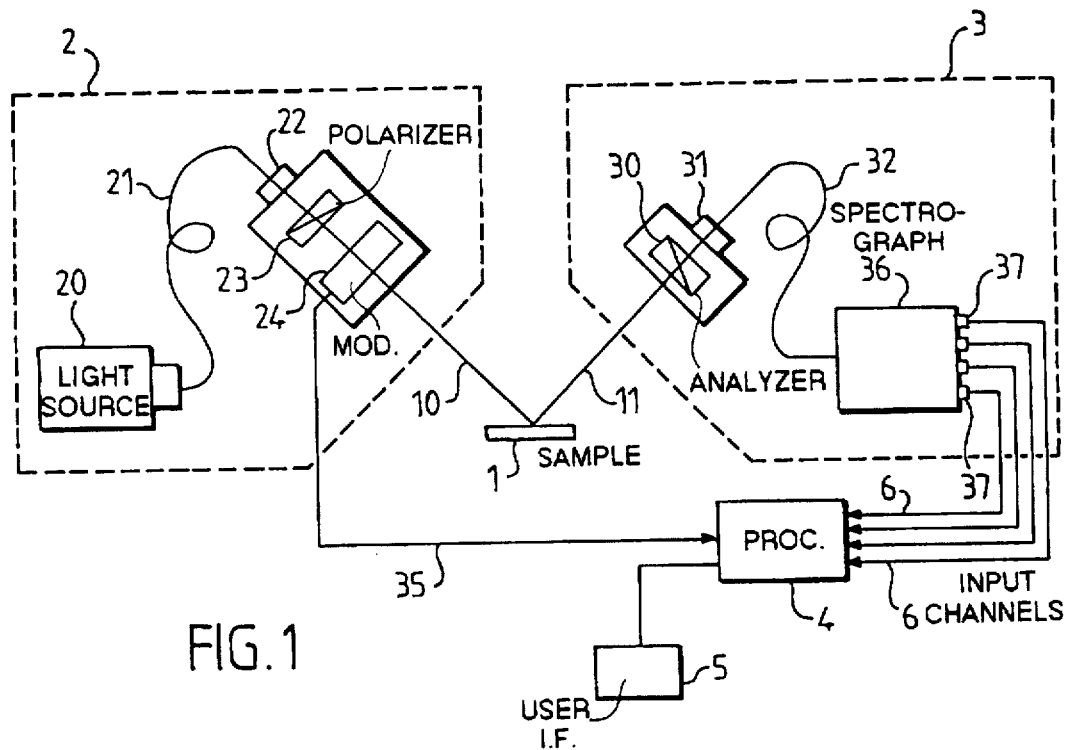
FIG. 1 is a schematic representation of a multi-detector ellipsometer according to the invention.

The multi-detector ellipsometer, represented in FIG. 1, is designed for the measurement of the physical parameters of a sample 1. It comprises an excitation group 2, an analysis group 3, an electronic processing unit 4, and a user interface 5.

The excitation group 2 comprises a luminous source 20 linked to an optical system 22 by means of an optical fiber 21, the optical system 22 directing a luminous beam emitted by the source 20 towards the sample 1. The excitation group 2 also includes a polarizer 23 followed by a phase modulator 24 between the optical system 22 and the sample 1. This phase modulator 24 typically consists of a bar of melted silica submitted to a periodical stress generated by a piezoelectric transducer. In this way, a phase shift modulated with time between two eigne-axes of this bar is created, thus modulating the polarization of the emerging luminous radiation.

The analysis group 3 includes an analyzer 30 analyzing a beam reflected by the sample 1, followed by an optical system 31 addressing the reflected beam on a spectrograph 36 through the intermediary of an optical fiber 32. The spectrograph 36 is arranged in such a way as to disperse a light on a series of photodetectors 37, being n in number, each of said photodetectors allowing the measurement of a wavelength.

They may be grouped in one-dimensional strips or two-dimensional arrays, and are linked to the electronic processing unit 4 respectively by connections or input channels 6. Each of the photodetectors 37 transforms the intensity of a detected flux into an electric signal.

The multi-detector spectroscopic ellipsometer of FIG. 1 thus permits simultaneous measurement of several wavelengths, a multiplexing of which may be carried out in the electronic processing unit 4. Said electronic processing unit 4 also receives a frequency and phase reference from the phase modulator 24 by a line 35.

The electronic processing unit 4 communicates with the user interface 5, which is typically a computer console. In practice, the electronic processing unit 4 may be connected to a computer network such as that commercialized under the name "Ethernet". When it is connected to an international network, maintenance work on the ellipsometer can be carried out, even at a great distance.

In operation, the luminous source 20 emits an incident luminous beam 10 in a given range of wavelengths, this beam being polarized linearly by the polarizer 23, then being submitted to a modulation by the phase modulator 24. The polarized incident luminous beam 10 being defined by a polarization vector, the phase modulator 24 introduces between perpendicular components of the polarization vector a phase shift depending on time according to a periodic variation of frequency Fm.

The polarized and modulated incident luminous beam 10 becomes, after reflection on the sample 1, a reflected beam 11 having an amplitude and a phase resulting from the physical properties of the sample 1. This reflected beam 11 is analyzed in the analyzer 30, then decomposed spectrally in the spectrograph 36. The photodetectors 37 then measure the fluxes of the reflected luminous beam 11 at different wavelengths. They produce respectively in the input channels 6, electric signals generated by the intensity of the fluxes, or measured analog signals 40. These signals 40 are received by the electronic processing unit 4.

The electronic processing unit 4 then calculates, from these measured analog signals 40, physical parameters 46 of the sample 1 such as the thickness of a film or a refraction index.

The phase-modulated spectroscopic ellipsometer, represented in FIG. 1, is advantageously used in an appliance for controlling the elaboration of films on a substrate. The sample 1 then consists of a substrate on which a deposit is made to grow by a known technique. The previously described ellipsometer is used for the purpose of controlling the film growth on the substrate. In this way, real-time in situ measurements are carried out without perturbing the growth process. Instead of a film growth, the elaboration may consist of an etching.

The user interface 5 makes it possible to supervise operations carried out by the electronic processing unit 4, by activating and/or controlling them, and to exchange information with it. It thus makes it possible to decide initializations and calculations, to define and transmit acquisition parameters and to retrieve results for visualization. It also provides the possibility of remote-maintenance of the electronic processing unit 4.

The acquisition parameters comprise, for example, measurement durations, numbers of acquisition points and types of activation.

Figure 2:
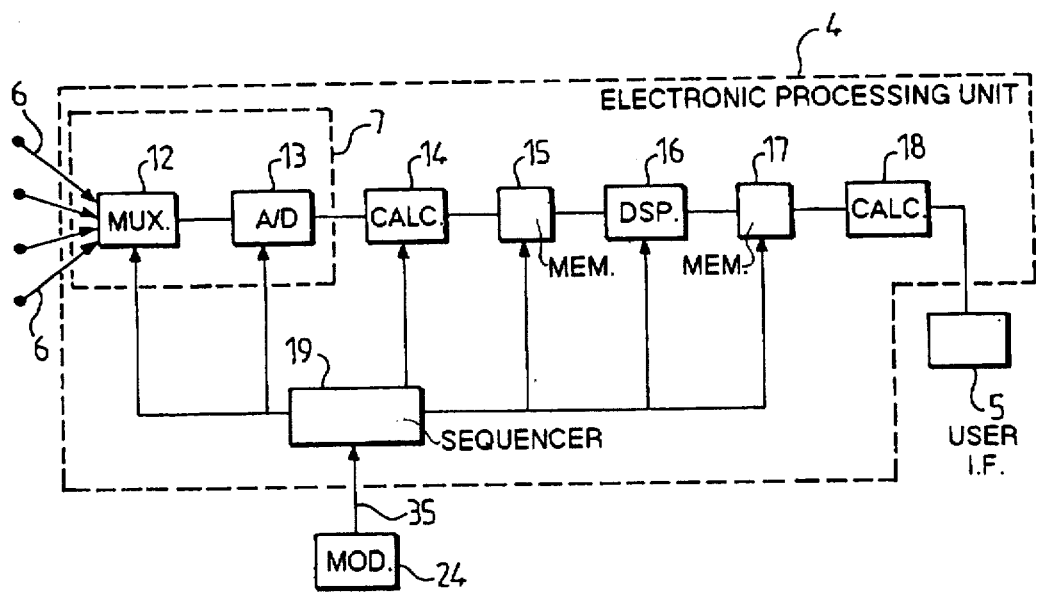
FIG. 2 is a schematic representation of the electronic processing unit of the ellipsometer represented in FIG. 1.

The electronic processing unit 4, as detailed in FIG. 2, comprises a multiplexing and digitization unit 7 at which the input channels 6 culminate, multiplexing and converting the measured analog signals 40 into a multiplexed digital signal. This unit 7 is made up of a multiplexer 12 and a digitizer 13, the output of the multiplexer 12 being linked to the input of the digitizer 13.

The multiplexer 12 is an analog multiplexer capable of multiplexing the measured analog signals 40 into a multiplexed analog signal, by switching successively on the input channels 6. The time required by the multiplexer 12 to switch from one input channel 6 to another and to establish the multiplexed analog signal in input of the digitizer 13 is of the order of 10 to 15 nanoseconds for present-day commercial circuits.

The digitizer 13, or analog-digital converter, is typically a currently available 12 bit digitizer, offering a conversion possibility of the order of 20 to 30 million samples per second.

The multiplexing and digitization unit 7 is designed to carry out, from each input channel 6, a sampling of P points per modulation period Tm. Each of the measured analog signals 40 is thus sampled according to a sampling period Tp equal to Tm/P.

The electronic processing unit 4 also comprises a first calculating unit 14 linked to the multiplexing and digitization unit 7. The purpose of said first calculating unit 14 is to carry out a preliminary filtering of the multiplexed digital signal, by integration on several modulation periods Tm associated to a cycle.

The number N of these modulation periods Tm of a cycle is chosen by a user according to the phenomena observed with the ellipsometer. An acquisition duration Ta equal to N×Tm corresponds to each cycle, the physical parameters 46 of the sample 1 being determined for this cycle immediately after the acquisition. The number N must therefore be sufficiently small to be capable of following measured expandable phenomena in real time on the sample 1. On the other hand, the greater N is, the greater the accuracy obtained for a given state of the sample 1. For example, to measure film growths on a substrate, it is advantageous that the number N should lie between 50 and 1,000,000 for a modulation frequency Fm of 50 kHz. The acquisition duration Ta then lies between 1 ms and 20 s. In order to obtain the physical parameters 46 of the sample 1 at a maximum rhythm, it is however possible to encompass a single modulation period Tm in each cycle.

The preliminary filtering of the multiplexed digital signal performed by the first calculating unit 14 employs a mean technique requiring an addition-accumulation, and producing results stored in acquisition points. Typically, each acquisition point has a storage capacity of 32 bits. The number of acquisition points for each input channel 6 is equal to the number P of sampling points per modulation period Tm.

The results calculated by the first calculating unit 14 are stored in a first double access memory 15. This first memory 15 acts as a buffer memory between the first calculating unit 14 and the next stage.

It communicates via its output with a digital signal processing (DSP) unit 16. The processing unit 16 may for example be the unit commercialized under the TMS 320C31 name by TEXAS INSTRUMENTS, capable of performing floating point operations on 32 bits. The purpose of the processing unit 16 is to carry out Fourier analyses on the results obtained by the first calculating unit 14 and stored in the first memory 15. It acquires data globally for each cycle, and thus receives at the end of each accumulation a set of values typically coded on 32 bits. The Fourier analyses are preferentially carried out by Fast Fourier Transform-type operations (FFT). They lead to Fourier parameters which are stored in a second double access memory 17.

The input of this second memory 17 is linked to the processing unit 16.

The output of the second memory 17 is linked to the second calculating unit 18 which is designed to calculate the physical parameters 46 from the Fourier parameters determined by the digital signal processing unit 16.

The electronic processing unit 4 also includes a sequencer 19 linked to the previously described elements 12, 13, 14 and 16 for the purpose of sending them synchronization signals. The sequencer 19 thus permits the piloting and synchronization of the processes. The sequencer 19 is linked to the phase modulator 24 by the reference line 35, and is synchronized in relation to the phase modulator 24 by means of a frequency multiplication system. This system consists typically of a Phase-Locked Loop (PLL). The sequencer 19 is thus capable of producing synchronization signals at a multiple frequency of the modulation frequency Fm.

Although it is not strictly necessary, in order to simplify the procedure each element of the electronic processing unit 4, with the exception of the sequencer 19, dialogues only with those elements which are directly adjacent to it. The functions of the sequencer 19 are not solely concerned with coordinating the acquisitions with the phase modulator 24. They also involve the launch of acquisitions, according to an activation coming, for example, from an external validation signal, and the start of the different sampling phases.

In practice, all the elements of the electronic processing unit 4, with the exception of the second calculating unit 18, are advantageously realized on a printed circuit board. In the embodiment example chosen, the first calculating unit 14 and at least a part of the sequencer 19 are grouped in a Field Programmable Gate Array (FPGA), a user being able to configure the functional characteristics of this type of integrated circuit. This field programmable gate array is capable of carrying out commands in parallel by working in pipe-lining mode as opposed to a sequential execution of operations. The digital signal processing unit 16 uses a floating point processor.

The second calculating unit 18, for its part, is part of a central unit, of the personal computer or PC type, managed in real time by a multi-task operating system. This central unit is capable of working according to different modes: acquisition, control, calculation, access to an external network, and statistics.

It thus makes it possible to collect data from the second memory 17, to make calculations on the data depending on the operating modes selected, and to archive the results for processing at a later date, such as an a posteriori analysis or statistics. It also controls the initialization of the ellipsometer and supervises its sampling.

The central unit includes a bus on which the printed circuit board containing the elements 12 to 17 and 19 may be connected. This said bus can be, for example, of one of the types commercialized under the ISA and PCI names. The printed circuit board is programmable from the central unit or by downloading via a network of the type known as "Ethernet". It is thus possible to define the configuration of the board in function of the desired operating mode, to load test configurations, to update versions depending on the evolution of the ellipsometer, and to carry out remote maintenance on site without manipulating the board.

The central unit comprising the second calculating unit 18 is capable of receiving several printed circuit boards such as the one previously described, all the boards being connected onto the bus of the central unit. In this way, greater amounts of information may be processed and correlated.

Moreover, the central unit may include printed circuit boards filling specific functions necessary to the working of the ellipsometer, such as positioning, obturation and supply commands.

In view of the current development and integration of fast components, the electronic processing unit 4 may advantageously comprise such components.

The electronic processing unit 4 may function independently without requiring a link with the user interface 5. In this case it carries out a succession of operations which are pre-recorded or defined by previous loading from a source system. At the end of the operation, it is in a position to transmit the results obtained to a network, in the direction of one or several end users. The electronic processing unit 4 may thus be considered as a complete system, known as an "embedded" system.

The electronic processing unit 4 may also be linked to another system, with a view, for example, to controlling an elaboration process. In particular, this linked use may be employed for depositing thin films.

The user interface 5 is itself capable of communicating not only with the electronic processing unit 4, but also with other applications, thereby making it possible to correlate information coming from several devices.

Figure 3:
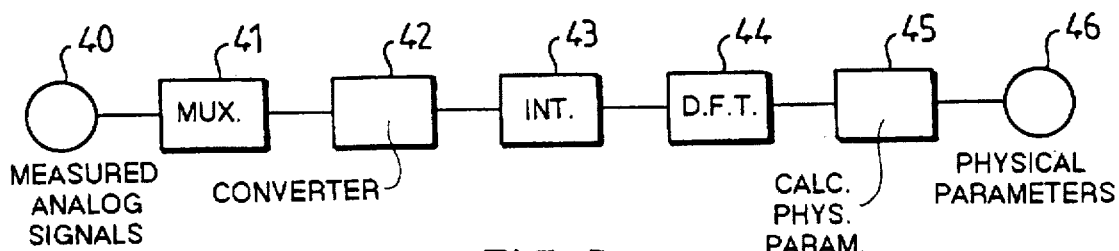
FIG. 3 is a synoptic diagram of the operations performed by the electronic processing unit represented in FIG. 2.

In operation, the following stages represented in FIG. 3 are performed successively by the electronic processing unit 4. In a first stage 41 of multiplexing, the measured analog signals 40 reaching the multiplexer 12 by the input channels 6 are multiplexed in a multiplexed analog signal. During a second stage 42 of digitization, the multiplexed analog signal is converted by the digitizer 13 into a multiplexed digital signal. In a third stage 43 of preliminary filtering, the multiplexed digital signal is integrated by the first calculating unit 14. The results of the preliminary filtering accumulated for an acquisition cycle in the first memory 15 are processed by the digital signal processing unit 16 during a fourth Fourier analysis stage 44. The processing unit 16 extracts components corresponding respectively to the input channels 6 and calculates, for each of the components, associated Fourier parameters. In standard fashion, the Fourier parameters calculated for each of the measured analog signals 40 consist of direct current components, at the frequency Fm and the frequency 2 Fm of these signals. The physical parameters 46 are next determined by the second calculating unit 18 from the Fourier parameters stored in the second memory 17, in the course of a fifth calculating stage 45 of the physical parameters 46. A description of these calculations is given in the previously cited article by B. DREVILLON.

Figure 4:
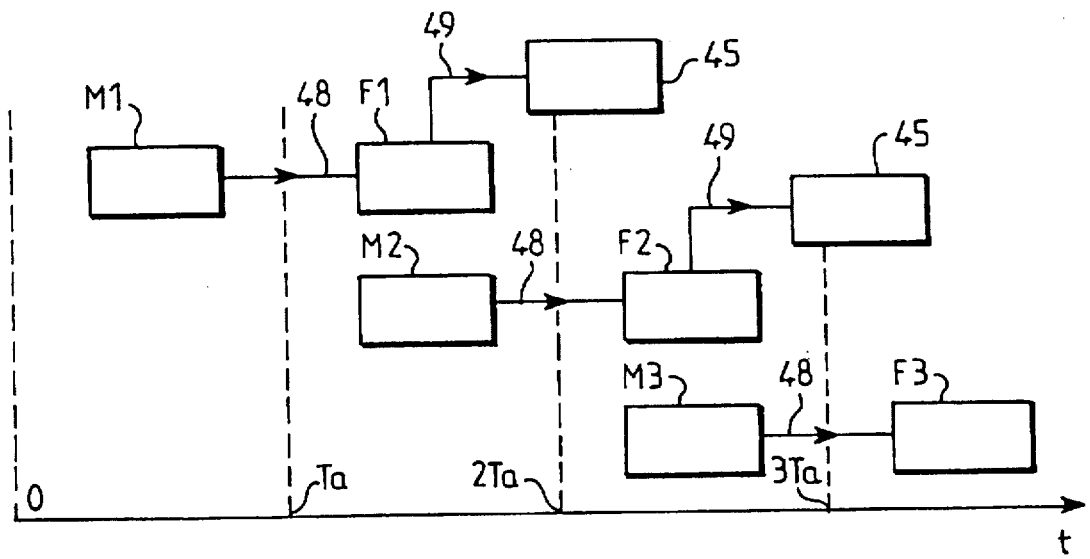
FIG. 4 shows the progression in time of the acquisition and processing operations carried out by the electronic processing unit represented in FIG. 2 over several cycles.

The sequencing of the different cycles, represented in simplified form in FIG. 4, shows how the stages described above succeed and overlap from one cycle to another. The stages of multiplexing 41, digitization 42 and preliminary filtering 43, taken together, are named Mi for the cycle number i, and the Fourier analysis stage 44 for this same cycle is named Fi.

After the launch of the measured analog signals 40 has been activated, the first acquisition cycle starts up. All the measured analog signals 40 coming from the n input channels 6 are then successively multiplexed, digitized and filtered beforehand, during the phase M1.

The results obtained are stored progressively by acquisition points in the first memory 15. The phase M1 has a duration approximately equal to the acquisition duration Ta, to a value of N×Tm, for all the operations during this phase M1 are carried out as and when the acquisitions are made.

At the end of the acquisition duration Ta, a first information transfer 48 is carried out from the first memory 15 as far as the digital signal processing unit 16. At the end of the transfer 48, the second acquisition cycle begins. The phase M2 thus takes place between the instants Ta and 2 Ta, the phase F1 of the first cycle being conducted during this duration. The number of data processed in the course of the phase F1 is generally small compared to the previous phase M1, due to the regrouping carried out by integration during the stage 43 of preliminary filtering, with the result that the processing duration available provides the opportunity to perform complex calculations.

An information transfer 49 of the second memory 17 towards the second calculating unit 18 finally allows the calculation of the physical parameters 46 sought during the stage 45. In the example of the chosen embodiment, this stage 45 is conducted independently of the previous M1 and F1 phases, for it is performed by the central unit. The transfer 49 of the Fourier parameters may therefore be carried out before the end of the second acquisition period Ta, and even before the end of the phase F1, as and when the Fourier parameters associated to the different input channels 6 become available.

At the instant 2 Ta concluding the acquisition of the measured analog signals 40 for the second cycle, the phase M2 being completed, the information transfer 48 is performed, and then the phase F2 begins at the same time as the acquisitions launching the phase M3 of the third cycle. All the operations described above are then reproduced identically with an incrementation of the number i of the cycle.

It will be noticed that the overlapping practiced during the succession of the cycles makes it possible to reduce the total duration of the operations to that of the acquisitions by the electronic processing unit 4 of the measured analog signals 40.

All these acquisitions are performed in parallel for all the input channels 6 for each cycle.

Figure 5:
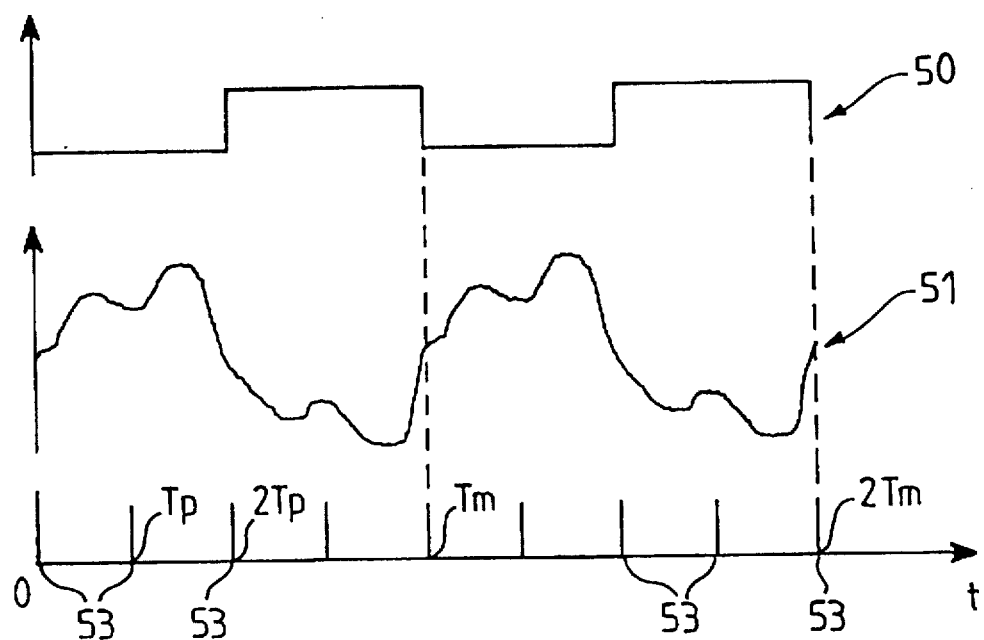
FIG. 5 represents the temporal evolutions of the modulation signal generated by the phase modulator of the ellipsometer represented in FIG. 1, of the signal measured in one of the input channels, and of the sampling carried out by the electronic processing unit of FIG. 2 on this input channel.

The phase modulator 24 produces in function of time t a reference signal 50 having for modulation period Tm, for example in strobe, as represented in FIG. 5. Following this modulation, the photodetectors 37 measuring fluxes of the luminous beam 11 at different wavelengths, generate in the input channels 6 measured analog signals 40 themselves admitting the modulation period Tm. As an illustration, the measured analog signal 51 obtained in one of the input channels 6 is considered (FIG. 5). The multiplexing and digitization unit 7 carries out on this measured analog signal 51 a sampling of P sampling points 53 on each modulation period Tm. In the example represented in FIG. 5, the number P has a value of 4. The measured analog signal 51 is thus sampled at a period Tp equal to Tm/P.

For each of the input channels 6, a sampling similar to the sampling period Tp is carried out, but with a time shift less than this sampling period Tp. The signals required for the control of the multiplexer 12 and the digitizer 13 are delivered by the sequencer 19. The sampling period Tp is divided into n equal parts (n being the number of input channels 6), which define a switching period Te with a value of Tp/n.

During each switching period Te, the multiplexer 12 acquires one of the measured analog signals 40 coming from one of the input channels 6. At the end of this time, said multiplexer 12 selects by switching the next input channel 6. In a sampling period Tp, the multiplexer 12 scans all the input channels 6. At each connection of the multiplexer 12 on an input channel 6, the digitizer 13 extracts a sampling point.

Figure 6:
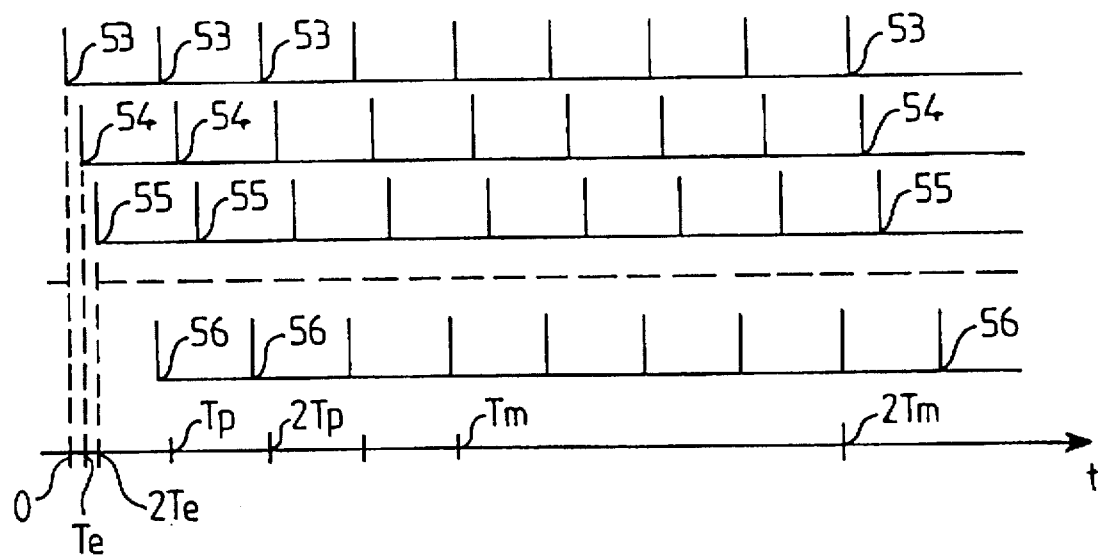
FIG. 6 shows the interlacing of the samplings carried out by the electronic processing unit of FIG. 2 respectively for the different input channels.

The succession of the samplings according to the different input channels 6 is therefore carried out in the following way, as represented in FIG. 6. At the start of the acquisitions, the multiplexing and digitization unit 7 selects a sampling point 53 on the measured analog signal 51 coming from the first of the input channels 6. After a switching period Te, the unit 7 switches onto the second of the input channels 6 and selects a sampling point 54 on the measured analog signal which comes from it. This operation is repeated for the third input channel and so on up to the nth input channel 6, for which the sampling points 55 and 56 are respectively selected. The multiplexer 12 then selects again the first of the input channels 6, so that the multiplexing and digitization unit 7 again produces a value of the measured analog signal 51 in another sampling point 53, at the end of a sampling period Tp from the launch of the acquisitions.

The unit 7 proceeds in the same way as previously indicated for the next (P−1) sampling periods Tp, until the complete running of a modulation period Tm, and then of N modulation periods Tm constituting the first cycle.

The acquisition period Ta corresponding to a cycle is independent of the number n of input channels 6, thanks to the parallelism of the operations. It is equal to N×Tm.

It will be noticed that, in the multiplexed digital signal from the multiplexing and digitization unit 7, the values from respectively the different input channels 6 are interlaced.

The multiple time shifts of the switching period Te obtained between the samplings of the different measured analog signals 40 are taken into account by the digital signal processing unit 16 by means of corrective terms depending on the number of the input channel 6 under consideration. These corrective terms are notably used in determining the phase of the Fourier components at the frequencies Fm and 2 Fm, in relation to the reference signal 50.

The successive acquisitions of the multiplexing and digitization unit 7 are controlled by the sequencer 19, which sends the synchronization signals at the switching period Te. The sequencer 19 produces these signals from the reference signal 50 of the phase modulator 24, by frequency multiplication.

In a representative example of application, the modulation frequency Fm has a value of 50 kHz, the number n of input channels 6 a value of 32 and the number P of points a value of 8. The digitizer 13 must therefore extract Fm×n×P values per second, that is to say, 12.8 million values per second. This speed is consistent with the capacities of the digitizer 13, which is capable of converting in the region of 20 to 30 million samples per second, taking into account the switching time of the multiplexer 12 and the time required to establish a signal in input of the digitizer 13. The switching period Te then has a value of approximately 78 ns.

The first calculating unit 14 thus receives information at a high rate, corresponding to one 12-bit data every 78 ns. On the other hand, the digital signal processing unit 16 receives information only after times equal to the acquisition duration Ta, usually greater than or equal to 1 Ms. This information is the result of the integration on a cycle of the values received by the first calculating unit 14, in order to obtain the mean values on a modulation period Tm. The digital signal processing unit 16 thus receives for each cycle P×n, that is to say 256, coded values on 32 bits.

The numerical values used in the example are for explanatory purposes only and are in no way limitative. In particular, the modulation frequency Fm, the number n of input channels 6, the number P of sampling points per modulation period Tm, as well as the resulting durations Tp and Te, may be very different. Thus, another valid embodiment with the same digitizer 13 consists in using a modulation frequency Fm equal to 100 kHz, 16 input channels 6, and 8 sampling points per input channel 6 and per modulation period Tm.

If the modulation frequency Fm is weak in relation to the capacities of the electronic processing unit 4, the conditions of acquisition may be modified so as to improve data processing by accumulating the sampling points, resulting in an improvement of the apparent resolution of the digitizer 13.

As an example, for a modulation frequency Fm of 2 kHz, 32 input channels 6 are used, and 128 sampling points per input channel 6 and per modulation period Tm are considered, these points being stored on 12 bits. By accumulating the 128 points in the form of 8 groups of 16, the real 12-bit resolution of the digitizer 13 is transformed into an apparent 16-bit resolution, for a Fourier analysis on 8 values.

Instead of connecting the multiplexing and digitization unit 7 to a new input channel 6 at each acquisition of a sampling point, several sampling points may be acquired between two switchings. The switching frequency Fe is in this case always a multiple of the modulation frequency Fm multiplied by the number n of input channels 6, but no longer necessarily by the number P of sampling points.

It is also possible to scan all the n input channels 6 only on several modulation periods Tm. The switching frequency Fe is in this case a multiple of the modulation frequency Fm multiplied by the number P, but no longer necessarily by the number n of input channels 6.

Clearly, a third possibility, consisting of both acquiring several sampling points between two switchings and scanning all the n input channels 6 on several modulation periods Tm, results in a switching frequency Fe which is now only a multiple of the modulation frequency Fm.

The solution adopted in the illustrative example is, however, optimal, assuming that the capacities of the multiplexer 12 are equal to the task, inasmuch as the acquisitions of the n input channels 6 are quasi-simultaneous.

The ellipsometer according to the invention may be completed by external means of excitation capable, for example, of sending an independent supplementary excitation optical beam on the sample 1 at a frequency which is distinct from the modulation frequency Fm. This excitation may also be of the electric or magnetic kind.

The presence of programmable circuits in the printed circuit board now makes it possible to adapt to a multiple modulation, simply by changing the sequence of logical operations managing the sequencer 19, irrespective of the relation between the different frequencies. The only condition required is that the demodulation must be compatible with the capacities of the multiplexing and digitization unit 7.

The multiplexing and digitization unit 7 may be realized in a different way from that presented here. Thus, a digitizer may be used per input channel 6, the digital signals obtained being next multiplexed by a digital multiplexer comprising an appropriate bus. However, this is more costly than the solution adopted, due to the fact that it necessitates the installation of a greater number of components, and is more difficult to realize, largely because of the need to possess a digital bus with sufficient capacity. In the example presented, this digital bus must be capable of being connected to 32 circuits sending converted information on 12 bits.

The two ways of realizing the multiplexing and digitization unit 7 may also be combined. In this case, the unit 7 comprises several analog multiplexers, each of them receiving a part of the input channels 6 and being linked to a digitizer. The digitizers are connected to the bus of a digital multiplexer. This intermediate solution is advantageous compared to the use of one digitizer per input channel for the same reasons as those given above. This solution, compared to the use of a single digitizer, will be necessary if the processing capacities of the digitizer are insufficient, particularly if there are too many input channels.

Rather than introduce time shifts between the samplings associated with the different input channels 6, it is possible to carry out the synchronous acquisition of all the input channels 6 by inserting a sampler-blocker between each of the input channels 6 and the multiplexer 12. However, the solution presented in the first instance keeps production costs to a minimum.

Whereas in the embodiment presented, the sequencer 19 is synchronized in relation to the phase modulator 24, another embodiment consists in equipping the electronic processing unit 4 with an internal clock delivering both the signals required to operate the unit and signals piloting external components such as a polarization modulator replacing the phase modulator 24. Thus the internal clock generates both the switching period Te, and the modulation period Tm by frequency division.

The user interface 5 may be used as a simple control tool, or even eliminated.

If the user so wishes, the behavior of the electronic processing unit 4 may be frozen in non volatile memory. In this case the unit becomes a system dedicated to a particular application and loses its programmable nature.

The realization of the elements 12 to 17 and 19 in a printed circuit board, and the realization of the second calculating unit 18 in a central unit, must be considered as preferential realizations without excluding other possibilities. Thus, the electronic processing unit 4 in its entirety may be integrated with the central unit of a computer, although this conception is more difficult to implement than that adopted in the example described above. The distribution chosen in the example presented, consisting of the use of a central unit of a computer for the second calculating unit 18, is nevertheless more judicious with regard to the variety of operations which can be carried out from Fourier parameters.

Other embodiments of the electronic processing unit 4, associating one or several printed circuit boards with one or several computers, may also be envisaged.

Although interest has focused up to now on a phase modulation, the scope of the technique corresponds more generally to polarization modulation ellipsometry.

In addition, the ellipsometer according to the invention may be used not only in spectroscopy, for analyzing a luminous beam returned by a sample along several wavelengths, but also in the sphere of imaging, the photodetectors 37 receiving parts of the returned beam 11 from different zones of the sample 1. Several synchronized incident beams lighting the sample 1 in different zones may also be used.

In another embodiment of the ellipsometer according to the invention, the returned beam 11 is broken down by a polarimeter into different polarization states. This embodiment is suited to measurements in the presence of light diffusion by the sample 1 or by a physical system.

More generally, the ellipsometer and the measuring process according to the invention are exploitable in situations when interest is taken in several parts of one or several luminous beams, each of these parts being measured by a photodetector 37.

We claim:

1. A multi-detector ellipsometer, comprising
   a) at least one luminous source emitting at least one incident luminous beam;
   b) at least one polarizer polarizing the incident luminous beam;
   c) at least one polarization modulator performing polarization modulation on the luminous beam at a modulation frequency;
   d) means for illuminating a sample with the incident luminous beam so as to produce a returned luminous beam that has a polarization state;
   e) at least one analyzer for analyzing the polarization state of the returned luminous beam;
   f) at least two photodetectors measuring flux of parts of the returned luminous beam and providing measured analog signals on input channels;

g) at least one electronic processing unit, linked to the input channels, and calculating physical parameters of the sample from the measured analog signals, the electronic processing unit including:
1) at least one multiplexing and digitization unit, multiplexing and converting the measured analog signals into a multiplexed digital signal, and switching successively on the input channels at a switching frequency;
2) a digital signal processing unit, responsive to the multiplexing and digitization unit, dissociating the multiplexed digital signal into components corresponding to respective input channels, and applying a discrete Fourier transform to the components to extract Fourier parameters;
3) a final calculating unit, responsive to the digital signal processing unit, for calculating the physical parameters from the Fourier parameters; and
4) a sequencer, responsive to the multiplexing and digitization unit and to the digital signal processing unit, for sending synchronization signals, the sequencer including means for ensuring that the switching frequency is a multiple of the modulation frequency.

2. The ellipsometer of claim 1, wherein:
the multiplexing and digitization unit produces values of the multiplexed digital signal at sampling points; and
the switching frequency is equal to the modulation frequency multiplied by a number of input channels and a number of sampling points per input channel and per modulation period.

3. The ellipsometer of claim 2, wherein the multiplexing and digitization unit includes:
a multiplexer, linked to the input channels, and multiplexing the measured analog signals into a multiplexed analog signal by switching successively on the input channels; and
a digitizer, linked to the multiplexer, and converging the multiplexed analog signal into the multiplexed digital signal.

4. The ellipsometer of claim 3, wherein the electronic processing unit includes:
a first calculating unit, responsive to the digitizer and to which the digital signal processing unit is responsive, and carrying out a preliminary filtering of the multiplexed digital signal by integrating over several modulation periods.

5. The ellipsometer of claim 1, further comprising:
means for providing supplementary external excitation of the sample that is capable of generating a supplementary modulation at an excitation frequency that is distinct from the modulation frequency of polarization.

6. The ellipsometer of claim 5, further comprising:
a clock that is external to the electronic processing unit and which generates the modulation frequency; and
a frequency multiplication that links the clock to the sequencer so that the sequencer generates the switching frequency from the modulation frequency.

7. The ellipsometer of claim 1, wherein the electronic processing unit includes:

an internal clock that generates the modulation frequency and the switching frequency.

8. The ellipsometer of claim 1, wherein the electronic processing unit includes:
at least one printed circuit board that includes at least one field programmable gate array.

9. The ellipsometer of claim 1, wherein the electronic processing unit further includes:
a pre-processing memory, located between the multiplexing and digitization unit and the digital signal processing unit, and storing the multiplexed digital signal for at least one modulation period and then providing the multiplexed digital signal to the digital signal processing unit.

10. The ellipsometer of claim 1, further comprising:
a user interface allowing connection of the electronic processing unit to a communication network.

11. A multi-detector ellipsometric measuring process for measuring physical parameters of a sample, comprising:
a) emitting at least one incident luminous beam;
b) polarizing the incident luminous beam;
c) modulating the incident luminous beam at a modulation frequency;
d) illuminating the sample with the incident luminous beam so that the sample produces a returned luminous beam that has a polarization state;
e) analyzing the polarization state of the returned luminous beam;
f) measuring flux of parts of the returned luminous beam with photodetectors that provide measured analog signals; and
g) performing operations on the measured analog signals with an electronic processing unit, to deduce the physical parameters, the operations including:
1) multiplexing and converting the measured analog signals into a multiplexed digital signal by switching the input channels at a switching frequency that is a multiple of the modulation frequency;
2) dissociating the multiplexed digital signal into components that correspond to respective input channels;
3) applying Fourier transforms to the components to extract Fourier parameters; and
4) calculating the physical parameters from the Fourier parameters.

12. The process of claim 11, further comprising:
performing a wavelength spectral decomposition on the returned luminous beam to produce the parts that are measured by the photodetectors.

13. The process of claim 11, further comprising:
performing a spatial decomposition on the returned luminous beam from different zones of the sample to produce the parts that are measured by the photodetectors.

14. The process of claim 11, further comprising:
performing a polarization decomposition on the returned luminous beam to produce the parts that are measured by the photodetectors.

* * * * *